(12) United States Patent
Tritthart et al.

(10) Patent No.: US 6,245,353 B1
(45) Date of Patent: Jun. 12, 2001

(54) SOLID, RAPIDLY DISINTEGRATING CETIRIZINE FORMULATIONS

(75) Inventors: Wolfram Tritthart, Wolfsberg/Karinthia; Mario André Piskering, St. Stefan/Karinthia, both of (AT)

(73) Assignee: ASTA Medica AG (DE)

( * ) Notice: Subject to any disclaimer, the term of this patent is extended or adjusted under 35 U.S.C. 154(b) by 0 days.

(21) Appl. No.: 09/277,403

(22) Filed: Mar. 26, 1999

(30) Foreign Application Priority Data

Mar. 31, 1998 (DE) .............................. 198 14 256

(51) Int. Cl.[7] ........................................ A61K 9/46
(52) U.S. Cl. .................... 424/466; 424/489; 514/784
(58) Field of Search .................... 424/466, 489, 424/465

(56) References Cited

U.S. PATENT DOCUMENTS 4,678,661  7/1987  Gergely et al. ............. 424/466
5,178,878  1/1993  Wehling et al. ............. 424/466
5,696,165  * 12/1997 Armitage et al. ............. 514/570

FOREIGN PATENT DOCUMENTS

94/10994   5/1994  (WO).
95/23591   9/1995  (WO).
95/34283  12/1995  (WO).

* cited by examiner

Primary Examiner—James M. Spear
(74) Attorney, Agent, or Firm—Gabriel P. Katona L.L.P.

(57) ABSTRACT

The present invention relates to a solid, effervescent, rapidly dissolving dosage form for oral administration, of (a) cetirizine or a pharmaceutically acceptable salt thereof, (b) an effervescent base comprising (i) at least one of (1) an organic edible acid and (2) a salt thereof, (ii) at least one of an alkali metal and an alkaline earth metal carbonate and bicarbonate, and (c) optionally a pharmaceutically acceptable auxiliary ingredient.

16 Claims, 1 Drawing Sheet

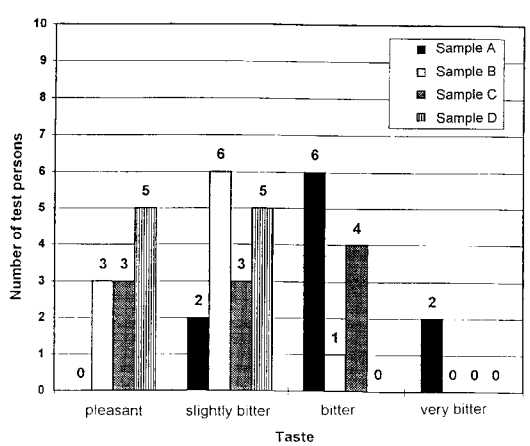

CONSUMER TASTE TEST
CETIRIZINE formulations

Using 10 test persons in a double-blind study
Instrument for data collection: Questionnaire Formulations tested:
Sample A = 10 mg of cetirizine + 60 ml of water
Sample B = 10 mg of cetirizine + "sodium base" + 60 ml of water
Sample C = 10 mg of cetirizine + "calcium base" (aroma 1) + 60 ml of water
Sample D = 10 mg of cetirizine + "calcium base" (aroma 2) + 60 ml of water In an aqueous solution, the pure active compound tastes very bitter. The study shows clearly that the bitter taste of cetirizine is masked well by the effervescent formulations according to the invention.

Figure 1

CONSUMER TASTE TEST
CETIRIZINE formulations

Using 10 test persons in a double-blind study

Instrument for data collection: Questionnaire

Formulations tested:

Sample A = 10 mg of cetirizine + 60 ml of water

Sample B = 10 mg of cetirizine + "sodium base" + 60 ml of water

Sample C = 10 mg of cetirizine + "calcium base" (aroma 1) + 60 ml of water

Sample D = 10 mg of cetirizine + "calcium base" (aroma 2) + 60 ml of water

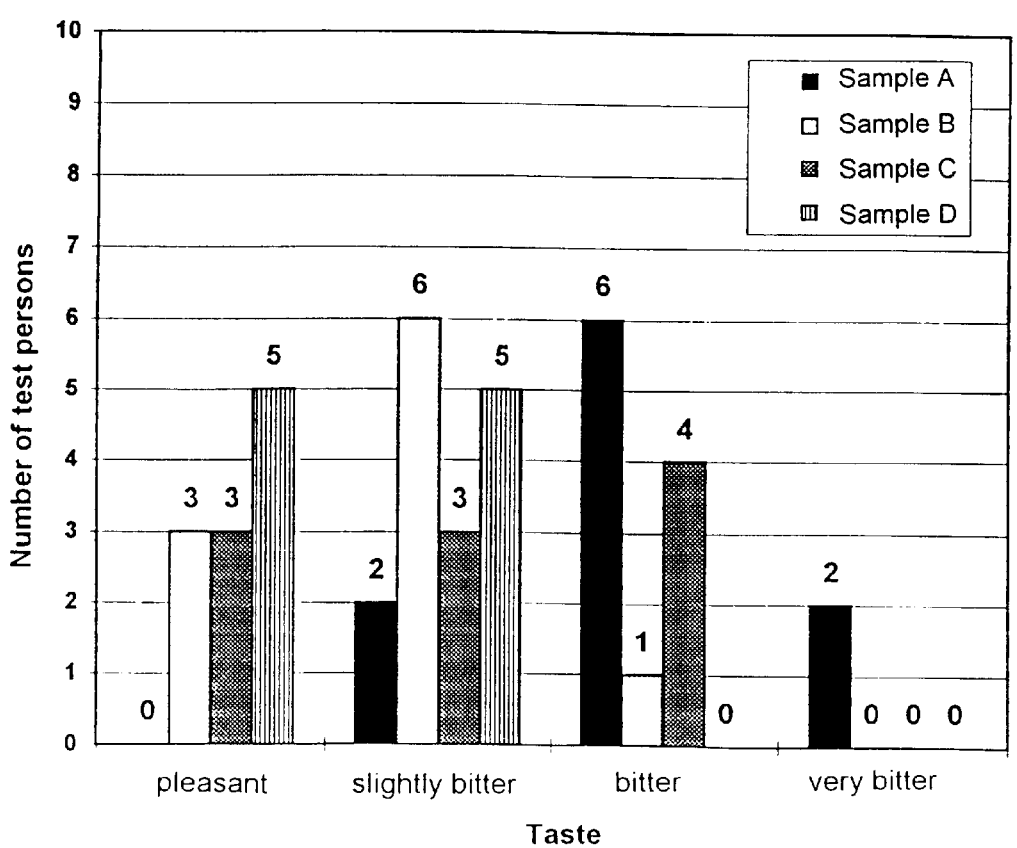

In an aqueous solution, the pure active compound tastes very bitter. The study shows clearly that the bitter taste of cetirizine is masked well by the effervescent formulations according to the invention.

SOLID, RAPIDLY DISINTEGRATING CETIRIZINE FORMULATIONS

FIELD OF THE INVENTION

The present invention relates to solid, rapidly disintegrating effervescent cetirizine formulations in the form of soluble tablets, dispersible tablets or soluble granules.

BACKGROUND

Cetirizine, [2-[(4-chlorophenyl phenylmethyl]-1-piperazinyl]ethoxy] acetic acid is a nonsedating type histamine $H_I$ receptor antagonist having antiallergic and spasmolytic action, and is described in European patents Nos. 058,146; 294,993; and 357,369; and also WO 92/02212 relates to cetirizine formulations for the controlled or continuous release of cetirizine in the form of tablets and capsules. Oral or nasal formulations, for example in the form of cough syrup, are disclosed in WO 94/08551.

Cetirizine solutions for administration at the eye and in the nose are described in European patent No. 605,203. Oral administration forms coated with at least one layer of a volatile aroma, such as are described in menthol WO 94/-25009, and freeze-dried dosage forms having a taste-masking matrix as is described in European patent No. 636,365.

European patent No. 548,356 claims multiparticulate tablets having a disintegration rate in the oral cavity or on the tongue of less than 60 seconds which contain the active ingredient in the form of coated microcrystals, particularly microgranules for masking the taste.

WO 95/07070 discloses effervescent granules for producing a pharmaceutical preparation based on calcium carbonate and citric acid, where from 5 to 20 parts by weight of the citric acid are replaced by at least one other edible acid, such as malic acid.

European patent No. 636,364 describes a dosage form which dissolves very quickly and which has active ingredient particles which are coated with a taste-masking substance, a water-soluble combinable carbohydrate and a binder. The tablet disintegrates in the mouth within 30 seconds after oral administration, so that the coated active ingredient particles can be swallowed by the patient before the active ingredient is released.

For example, mannitol, dextrose or lactose are the carbohydrates used, and for example, cellulose acetate or hydroxypropylmethylcellulose are used for masking taste.

European patent No. 525,388 discloses lozenges or chewable tablets containing the dibasic alkali metal and/or alkaline earth metal salt of a tribasic edible organic acid, preferably an edible organic acid, more specifically citric acid, such as malic acid, which is only partly converted into the alkali metal and/or alkaline earth metal salt, and also to auxiliary ingredients. It is thus intended to avoid the stale aftertaste of known lozenges or chewable tablets, in particular the prevention of the chalky taste of lozenges or chewable tablets containing mineral substances. No reference is made to any possibility of relieving a bitter aftertaste.

The active ingredient cetirizine hydrochloride has a very bitter taste and is not particularly suitable for rapidly disintegrating, solid preparations. Consequently, effervescent cetirizine formulations are not known in the prior art.

There is a need to introduce on the market effervescent pharmaceutical preparations in the form of soluble and dispersible tablets based, in particular, on a calcium-containing base. Certain elderly people may have problems with taking tablets, and there are many patients who have difficulties in swallowing. Certain rapidly disintegrating effervescent formulations have the additional advantage of portability without any liquids.

The simultaneous intake of the mineral calcium with antihistamines is also desirable for the treatment of allergies.

Masking the bitter taste of cetirizine causes particular problems. Thus, an aqueous solution of cetirizine hydrochloride has an unpleasant bitter taste. By adding suitable taste-masking substances, as described, for example, in European patent No. 636,364 and in U.S. Pat. No. 5,178,878, the preparation is complicated, and the dispersibility of microencapsulated active ingredients is considerably reduced. It is a further disadvantage that, in addition to the actual active ingredient, a large number of auxiliary ingredients are required for preparing such a formulation.

Film-coated tablets and oral solutions are available in which the film layer masks the bitter taste. The solutions contain large amounts of sorbitol flavorant (450 mg of sorbitol per mg of cetirizine).

Effervescent preparations of various active ingredients and vitamins are generally known per se in the prior art. These effervescent preparations generally contain an agent which is capable of releasing $CO_2$, and an agent which induces the release of $CO_2$.

BRIEF DESCRIPTION OF THE DRAWING

The invention is described in greater detail hereinbelow, with reference being had to the sole FIGURE of the drawing illustrating the bitter taste of cetirizine, and its elimination by the present invention.

BRIEF DESCRIPTION OF THE INVENTION

It is the object of the present invention to provide novel and therapeutically advantageous solid, rapidly disintegrating effervescent formulations of cetirizine.

The present invention is a solid, effervescent, rapidly dissolving dosage form for oral administration, of (a) cetirizine or a pharmaceutically acceptable salt thereof, (b) an effervescent base comprising at least one of (i) at least one of (1) an organic edible acid and (2) a salt thereof, (ii) at least one of an alkali metal and an alkaline earth metal carbonate and bicarbonate, and (c) optionally a pharmaceutically acceptable auxiliary ingredient.

The development of the present invention, of a solid, rapidly disintegrating cetirizine formulation was unexpected in view of the bitter taste of cetirizine. Our own investigations have shown, for example, that 10 mg of cetirizine, dissolved in 60 ml of water, has a bitter taste (FIG. 1). If the formulation according to the present invention is dissolved in the same amount of water, the solution has a pleasant taste and can be taken by the patient without any problems, thus considerably improving compliance.

A solution or suspension is formed by adding water to the soluble or dispersible tablets or soluble granules, with evolution of $CO_2$ gas. The resulting effervescent solution or suspension can be taken very easily, even by patients who have difficulties swallowing. Surprisingly, this solution already has a pleasant taste. This becomes evident particularly in the case of calcium-containing effervescent preparations in soluble form.

The rapidly disintegrating tablet can also be administered so that it directly disintegrates in the mouth. A rapid release of the active ingredient is of particular importance here, to ensure a rapid onset of action.

Effervescent agents capable of releasing $CO_2$ which are suitably employed in connection with the present invention include alkali metal carbonates or alkali metal bicarbonates, such as sodium carbonate or sodium bicarbonate. Agents for inducing $CO_2$ release which are suitably employed are edible organic acids, or their acidic salts, which are present in solid form and which can be formulated with the cetirizine active ingredient and the other auxiliary ingredients to provide granules or tablets, without premature evolution of $CO_2$. Edible organic acids which can be so used include for example, tartaric acid, malic acid, fumaric acid, adipic acid, succinic acid, ascorbic acid, maleic acid or citric acid. Pharmaceutically acceptable acidic salts include, for example, salts of polybasic acids which are present in solid form and in which at least one acid function is still present, such as sodium dihydrogen or disodium hydrogen phosphate or monosodium or disodium citrate.

It has now been surprisingly found that the sole use of an effervescent system, in particular a system based on calcium, leads to a masking of the otherwise bitter taste of the active ingredient cetirizine.

No complicated coating of the individual crystals of the active ingredient for masking the bitter taste of cetirizine is necessary when using the present invention. Thus, it is possible, for the first time, to provide effervescent preparations of cetirizine, which is very effective for allergic disorders.

Cetirizine is an organic acid which can lead to stimulation of the $H_2$ receptors and consequently to an increase in the secretion of gastric juices. The buffer action of the effervescent formulation according to the invention can contribute to avoiding any side-effects.

The invention thus suitably provides effervescent cetirizine formulations having an effervescent base comprising (a) a mixture of calcium carbonate with an organic edible acid; (b) a mixture of calcium carbonate, sodium carbonate, sodium bicarbonate and an organic edible acid; or (c) a mixture of sodium bicarbonates, sodium carbonate and an organic edible acid.

The soluble or dispersible cetirizine tablet or the soluble granules comprises from about 5 mg to about 20 mg cetirizine and from about 50 mg to about 5000 mg, suitably from about 500 mg to about 3000 mg of an effervescent base.

The effervescent base suitably comprises from about 100 mg to about 500 mg calcium ions as calcium carbonate, and from about 20 mg to about 1500 mg citric acid and/or its salts. In a further suitable embodiment, the effervescent base comprises from about 50 mg to about 2000 mg sodium bicarbonate, from about 20 mg to about 200 mg of sodium carbonate and from about 20 mg to about 1500 mg citric acid and/or from about 20 mg to about 500 mg tartaric acid.

A further suitable composition of the effervescent base comprises from about 50 mg to about 500 mg sodium bicarbonate, from about 20 mg to about 100 mg sodium carbonate, and from about 50 mg to about 750 mg calcium carbonate and from about 100 mg to about 1500 mg of citric acid.

When dispersing the dispersible cetirizine tablet of the invention in water, there is also a formation of $CO_2$ which accelerates the disintegration of the tablet even to a greater extent. However, a reduced effervescent activity is observed here, compared to the soluble tablet.

The soluble/dispersible tablet can be prepared by known processes for preparing effervescent bases. In the segregated-bed process, the acidic components are granulated with a solution of, for example, citric acid in water or polyvinylpyrrolidone in water or alcohol. It is also possible to admix directly tablettable calcium carbonate for the calcium component. Sodium carbonate/bicarbonate and alkaline earth metal carbonate components can also be granulated separately. The other tabletting auxiliaries are incorporated homogeneously and the material is tabletted using an appropriate press.

However, it is also possible to obtain the appropriate product by other processes, such as alcoholic granulation of acidic and alkaline components with binder solutions, for example PVP or sugar alcohols. Other granulation processes, such as, for example, topogranulation can also be used.

The cetirizine formulations according to the present invention can additionally include aromas and sweeteners and also conventional pharmaceutical auxiliary ingredients, such as polyethylene glycol, sodium benzoate, adipic acid and silica.

The formulations according to the invention are to be illustrated in more detail by the following examples.

Example 1 Effervescent tablet

|  | mg |
|---|---|
| Cetirizine HCl | 10 |
| Effervescent base | 890 |
| Mannitol FG | 60 |
| Pharmatose DCL 21 | 70 |
| Peppermint aroma | 10 |
| Total | 1040 |
| The effervescent base contains: | |
| Citric acid | 558.5 |
| Sodium bicarbonate | 200 |
| Sodium carbonate | 100 |
| Sodium citrate | 0.5 |
| Ascorbic acid | 25 |
| Sodium saccharin | 6 |
| Total | 890 |

Example 2 Soluble Tablet

|  | mg |
|---|---|
| Cetirizine | 10 |
| Sodium bicarbonate | 200 |
| Citric acid | 443 |
| Ascorbic acid | 25 |
| Sodium carbonate | 100 |
| Sodium saccharin | 6 |
| Mannitol | 60 |
| Lactose | 70 |
| Total | 914 |

Example 3 Soluble granules

|  | mg |
|---|---|
| Cetirizine | 10 |
| Sodium bicarbonate | 200 |

Example 3 Soluble granules

|  | mg |
|---|---|
| Citric acid | 730 |
| Calcium carbonate | 230 |
| Ascorbic acid | 25 |
| Sodium carbonate | 50 |
| Sodium saccharin | 4 |
| Mannitol | 60 |
| Lactose | 70 |
| Total | 1379 |

Example 4 Soluble tablet

|  | mg |
|---|---|
| Cetirizine | 5 |
| Sodium bicarbonate | 200 |
| Tartaric acid | 454 |
| Sodium carbonate | 100 |
| Sodium saccharin | 6 |
| Mannitol | 100 |
| Lactose | 40 |
| Total | 905 |

Example 5 Soluble tablet

|  | mg |
|---|---|
| Cetirizine | 10 |
| Sodium bicarbonate | 186 |
| Citric acid | 491 |
| Calcium carbonate | 130 |
| Aspartame | 6 |
| Sodium carbonate | 35 |
| Mannitol | 120 |
| Total | 978 |

Example 6 Soluble granules

|  | mg |
|---|---|
| Cetirizine | 10 |
| Calcium carbonate | 750 |
| Citric acid | 805 |
| Avicel | 42 |
| Mannitol | 625 |
| Maltodextrin | 15 |
| Aspartame | 3 |
| Aroma | 20 |
| Total | 2270 |

Example 7 Dispersible tablet

|  | mg |
|---|---|
| Cetirizine | 5 |
| Calcium carbonate | 500 |
| Polyvinylpyrrolidone | 20 |
| Citric acid | 270 |
| Avicel | 20 |
| Maltodextrin | 18 |
| Xylitol | 500 |
| Aspartame | 2 |
| Sodium saccharin | 1 |
| Aroma | 15 |
| Maize starch | 60 |
| Total | 1411 |

Example 8 Dispersible Tablet

|  | mg |
|---|---|
| Cetirizine | 10 |
| Calcium carbonate | 500 |
| Polyvinylpyrrolidone | 17 |
| Citric acid | 160 |
| Avicel | 15 |
| Mannitol | 430 |
| Maltodextrin | 18 |
| Aspartame | 2 |
| Aroma | 15 |
| Total | 1167 |

Example 9 Dispersible tablet

|  | mg |
|---|---|
| Cetirizine | 10 |
| Calcium carbonate | 300 |
| Citric acid | 32 |
| Avicel | 17 |
| Mannitol | 250 |
| Maltodextrin | 6 |
| Aspartame | 1 |
| Hydrogenated castor oil | 21 |
| Aroma | 8 |
| Total | 645 |

Example 10 Chewable dispersible tablet

|  | mg |
|---|---|
| Cetirizine | 5 |
| Calcium carbonate | 750 |
| Ethocel | 37 |
| Aerosil | 100 |
| Mannitol | 1130 |
| Citric acid | 123 |
| Maltodextrin | 23 |
| Avicel | 87 |
| Aspartame | 5 |

Example 10 Chewable dispersible tablet

|  | mg |
|---|---|
| Peppermint aroma | 8 |
| Orange aroma | 70 |
| Total | 2338 |

Example 11 Chewable dispersible tablet

|  | mg |
|---|---|
| Cetirizine | 10 |
| Calcium carbonate | 750 |
| Ethocel | 37 |
| Aerosil | 100 |
| Mannitol | 1130 |
| Citric acid | 123 |
| Maltodextrin | 23 |
| Avicel | 87 |
| Aspartame | 5 |
| Peppermint aroma | 8 |
| Orange aroma | 70 |
| Total | 2343 |

Example 12 Chewable dispersible tablet

|  | mg |
|---|---|
| Cetirizine | 5 |
| Calcium carbonate | 750 |
| Eudragit E | 37 |
| Aerosil | 100 |
| Mannitol | 1130 |
| Citric acid | 123 |
| Maltodextrin | 23 |
| Avicel | 87 |
| Aspartame | 5 |
| Peppermint aroma | 8 |
| Orange aroma | 70 |
| Total | 2338 |

Example 13 Chewable dispersible tablet

|  | mg |
|---|---|
| Cetirizine | 10 |
| Calcium carbonate | 750 |
| Ethocel | 37 |
| Aerosil | 100 |
| Mannitol | 1130 |
| Citric acid | 123 |
| Maltodextrin | 23 |
| Avicel | 87 |
| Aspartame | 5 |
| Peppermint aroma | 8 |
| Orange aroma | 70 |
| Total | 2343 |

We claim:

1. A solid, effervescent, rapidly dissolving dosage form for oral administration, which comprises
   (a) cetirizine or a pharmaceutically acceptable salt thereof,
   (b) an effervescent base comprising
      (i) at least one of (1) an organic edible acid and (2) a salt thereof,
      (ii) at least one of an alkali metal and an alkaline earth metal carbonate and bicarbonate, and
   (c) optionally a pharmaceutically acceptable auxiliary ingredient.

2. The dosage form of claim 1, in the form of a soluble tablet, dispersible tablet, or soluble granule.

3. The dosage form of claim 1, wherein the amount of cetirizine or of its pharmaceutically acceptable salt in each dose of the dosage form is from about 5 mg to about 20 mg calculated as cetirizine, the amount of the effervescent base in each dose is from about 50 mg to about 5,000 mg.

4. The dosage form of claim 3, wherein the amount of said effervescent base per dose is from about 500 mg to about 3000 mg.

5. The dosage form of claim 1, wherein said effervescent base comprises a mixture of sodium bicarbonate, sodium carbonate and an organic edible acid.

6. The dosage form of claim 3, wherein said effervescent base comprises a mixture of sodium bicarbonate, sodium carbonate and an organic edible acid.

7. The dosage form of claim 5, wherein the effervescent base comprises from about 50 mg to about 2000 mg sodium bicarbonate, from about 20 mg to about 200 mg sodium carbonate, and from at least one of (i) from about 20 mg to about 1500 mg citric acid, and (ii) from about 20 mg to about 500 mg tartaric acid.

8. The dosage form of claim 1, wherein said effervescent base comprises a mixture of calcium carbonate and an organic edible acid.

9. The dosage form of claim 3, wherein said effervescent base comprises a mixture of calcium carbonate and an organic edible acid.

10. The dosage form of claim 8, wherein said effervescent base comprises from about 100 mg to about 500 mg calcium ions in the form of calcium carbonate, and at least one of (i) from about 20 mg to about 1500 mg citric acid, and (ii) at least one citrate.

11. The dosage form of claim 10, wherein said effervescent base comprises a mixture of calcium carbonate, sodium bicarbonate, sodium carbonate and an organic edible acid.

12. The dosage form of claim 11, wherein said effervescent base comprises from about 50 mg to about 500 mg sodium bicarbonate, from about 20 mg to about 100 mg sodium carbonate, from about 50 mg to about 750 mg calcium carbonate, and at least one of (i) from about 100 mg to about 1500 mg citric acid and (ii) at least one citrate.

13. The dosage form of claim 1, wherein said effervescent base comprises at least one of (i) an organic edible acid and (ii) a salt thereof, said acid being at least one of tartaric acid, malic acid, fumaric acid, adipic acid, succinic acid, ascorbic acid, maleic acid, and citric acid.

14. The dosage form of claim 1, wherein said effervescent base comprises an the organic edible acid or a salt thereof, wherein said organic acid is citric acid.

15. The dosage form of claim 1, further comprising one or more of an aroma, sweetener, and a pharmaceutical auxiliary ingredient.

16. The dosage form of claim 15, wherein said auxiliary ingredient is at least one of polyethylene glycol, sodium benzoate, adipic acid, and silica.

* * * * *